United States Patent
Tunmu et al.

(10) Patent No.: US 10,126,352 B1
(45) Date of Patent: Nov. 13, 2018

(54) METHOD FOR ENHANCING STABILITY, ROBUSTNESS AND THROUGHPUT OF SEMICONDUCTOR DEVICE TEST MACHINES IN LOW TEMPERATURE CONDITIONS

(71) Applicant: Ambarella, Inc., Santa Clara, CA (US)

(72) Inventors: Chia Chieh Tunmu, Taoyuan (TW); Kun-Jung Kuo, Hsinchu County (TW)

(73) Assignee: Ambarella, Inc., Santa Clara, CA (US)

( * ) Notice: Subject to any disclaimer, the term of this patent is extended or adjusted under 35 U.S.C. 154(b) by 176 days.

(21) Appl. No.: 15/202,786

(22) Filed: Jul. 6, 2016

(51) Int. Cl.
G01R 31/26 (2014.01)
G01N 27/04 (2006.01)

(52) U.S. Cl.
CPC ....... *G01R 31/2601* (2013.01); *G01N 27/048* (2013.01)

(58) Field of Classification Search
CPC ........................... G01R 31/2601; G01N 27/048
USPC ............... 324/500, 527–531, 750.01–754.11, 324/756.02, 756.07, 757.02, 763.01, 324/76.11, 125, 465, 207.13, 234–247, 324/200
See application file for complete search history.

(56) References Cited

U.S. PATENT DOCUMENTS

| | | | |
|---|---|---|---|
| 5,892,367 A | 4/1999 | Magee et al. | 324/760 |
| 6,703,852 B1 | 3/2004 | Feltner | 324/754 |
| 2004/0216536 A1* | 11/2004 | Park | G01R 31/2867 73/865.6 |
| 2006/0194352 A1* | 8/2006 | Peng | G01R 31/2877 438/14 |
| 2015/0185281 A1* | 7/2015 | Diglio | G01R 31/2893 324/750.24 |

OTHER PUBLICATIONS

Haihui Tan et al., Experimental study on defrosting mechanism of intermittent ultrasonic resonance for a finned-tube evaporator, Experimental Thermal and Fluid Science 52 (2014), pp. 308-317.

* cited by examiner

*Primary Examiner* — Melissa Koval
*Assistant Examiner* — Trung Nguyen
(74) *Attorney, Agent, or Firm* — Christopher P. Maiorana, PC

(57) ABSTRACT

An apparatus includes a platform, a test board mounted on the platform, and a test socket attached to the test board. The test socket may be configured to apply test signals to and receive test responses from a semiconductor device under test. The platform may be configured to utilize ultrasonic vibrations to inhibit frost formation between the semiconductor device under test and a test header providing a low temperature test condition.

18 Claims, 6 Drawing Sheets

US 10,126,352 B1

METHOD FOR ENHANCING STABILITY, ROBUSTNESS AND THROUGHPUT OF SEMICONDUCTOR DEVICE TEST MACHINES IN LOW TEMPERATURE CONDITIONS

FIELD OF THE INVENTION

The invention relates to semiconductor device test systems generally and, more particularly, to a method and/or apparatus for enhancing stability, robustness and throughput of semiconductor device test machines in low temperature conditions.

BACKGROUND

Semiconductor devices need to be tested at many different temperature conditions to meet quality concerns. Low temperature conditions during a semiconductor device test are obtained by cooling the semiconductor device using cold air or through contact with a test header that is maintained at a low temperature. Low temperature testing using conventional techniques can result in formation of frost. The frost is produced from moisture in the air and the low temperature of the test header. The frost can cause the semiconductor device to adhere to the test header. Detaching a stuck semiconductor device from the test header can damage a surface of the semiconductor device and/or the test header. Thus, frost formation can impact test stability, efficiency and throughput.

Existing techniques to remove the frost or suppress the frosting at low temperatures include dry air, physical separation, and temperature control. The dry air technique continuously pours dry air into the test room, which can decrease the relative humidity to suppress frost formation. However, as the test environment is generally not a closed space, the relative humidity is very difficult to keep constant. The frost suppression using dry air can be ineffective. The physical separation technique pushes out a separator through the test header. The test header has one or two holes. Through the holes, the separator can physically detach the semiconductor device from the test header. However, such a brute-force method of detaching the semiconductor device can break the device surface and, therefore, is not cost effective. The temperature control technique adopts test headers that are equipped with a heating scheme. The heating scheme can remove the frost on the test header and the semiconductor device. However, it takes longer to remove frost by heating and then cooling down the test system to continue the test, which can drastically increase the test duration. This is also not cost effective.

It would be desirable to implement a method for enhancing stability, robustness and throughput of semiconductor device test machines in low temperature conditions.

SUMMARY

The invention concerns an apparatus including a platform, a test board mounted on the platform, and a test socket attached to the test board. The test socket may be configured to apply test signals to and receive test responses from a semiconductor device under test. The platform may be configured to utilize ultrasonic vibrations to inhibit frost formation between the semiconductor device under test and a test header providing a low temperature test condition.

BRIEF DESCRIPTION OF THE FIGURES

Embodiments of the invention will be apparent from the following detailed description and the appended claims and drawings in which:

DETAILED DESCRIPTION OF THE EMBODIMENTS

Embodiments of the present invention include providing a method for enhancing stability, robustness and throughput of semiconductor device test machines in low temperature conditions that may (i) provide higher defrosting efficiency, (ii) be cost effective, (iii) prevent damage to a semiconductor device under test due to frost, (iv) use ultrasonic vibration to effectively restrain initial frost nucleation and frost growth, (v) adjust defrosting strength based on humidity of the test machine environment, (vi) be implemented in an automatic test line, (vii) be implemented in a standalone test bench, and/or (viii) be implemented as one or more integrated circuits.

Figure 1:
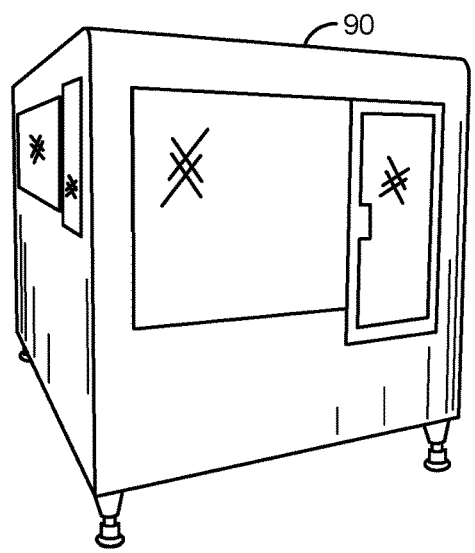
FIG. 1 is a diagram illustrating an integrated circuit test handler in which a system in accordance with an embodiment of the invention may be implemented.

Referring to FIG. 1, a diagram of an integrated circuit test handler is shown illustrating a context in which a system in accordance with an embodiment of the invention may be implemented. In various embodiments, a system and/or method in accordance with an embodiment of the invention may be implemented as part of a larger test machine (e.g., in an integrated circuit test handler 90) that is part an automatic test line or a standalone test bench. In various embodiments, the integrated circuit test handler 90 may comprise multiple instances of a test system in accordance with an embodiment of the invention, allowing parallel testing of a plurality of semiconductor devices. The integrated circuit test handler 90 is generally configured to provide low temperature test conditions for the semiconductor devices under test. In an example, the integrated circuit test handler 90 may include one or more test headers for providing low temperature conditions through contact with the semiconductor devices under test.

Figure 2:
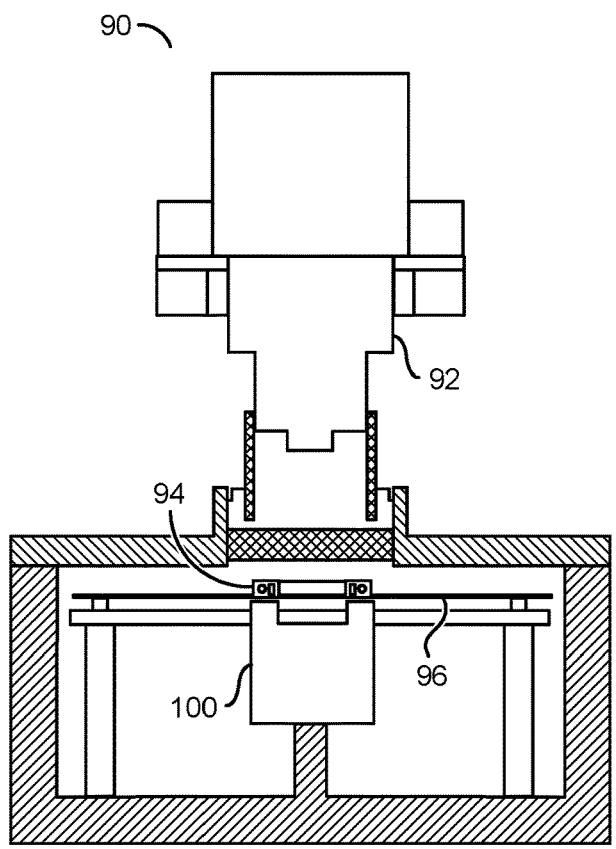
FIG. 2 is a diagram illustrating a system in accordance with an embodiment of the invention positioned below a thermal test header within the integrated circuit test handler of FIG. 1.

Referring to FIG. 2, a diagram is shown illustrating a test system instance in accordance with an embodiment of the invention. During testing, a thermal test header 92 of the test machine 90 is generally located above a test assembly comprising a test socket 94, a test board 96, and a platform 100. In an example, a device under test (DUT) is placed in the test socket 94 and the thermal test header 92 is lowered until contact is made with the DUT. The thermal test header 92 is chilled to provide a low temperature test condition. The test header 92 may be implemented using conventional techniques. The platform 100 is implemented in accordance with an embodiment of the invention to inhibit frost formation between the DUT and the test header 92.

Figure 3:
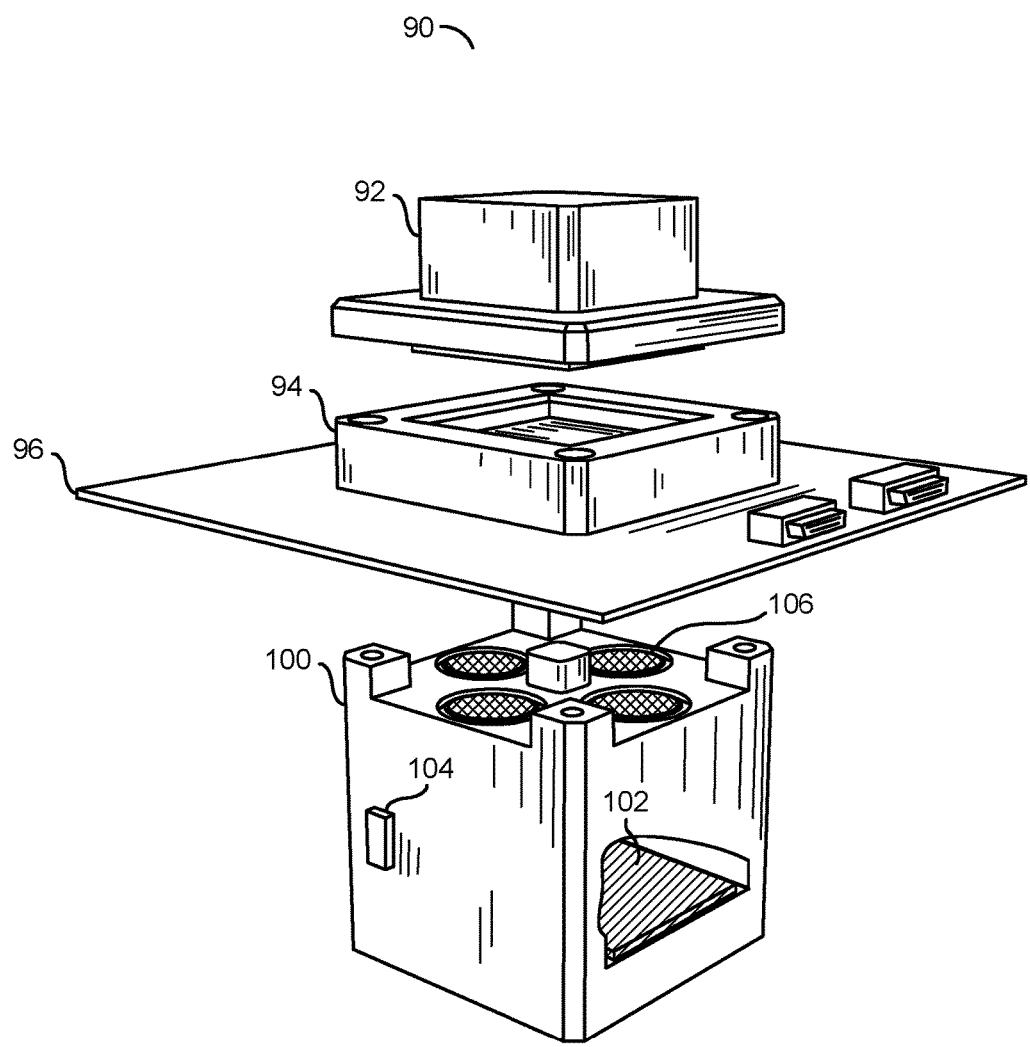
FIG. 3 is a diagram illustrating an example implementation of a platform in accordance with an example embodiment of the invention.

Referring to FIG. 3, a diagram is shown illustrating components of the test system 90 in accordance with an example embodiment of the invention. The thermal test header 92 may be separate from or part of a pick and place handler. The thermal test header 92 is generally configured to provide low temperature conditions for the semiconductor device under test located within the test socket 94. The test socket 94 is mounted (e.g., soldered, etc.) to the test board 96. The test socket 94 is configured to apply test signals to and receive test responses from the semiconductor device under test. The test board 96 is configured to mount between the test socket 94 and the platform 100 in a manner which allows the platform 100 to project vibrations in the ultrasonic range to an interface (e.g., contact plane) between the device under test and the test header 92. In various embodiments, the test board 96 may be connected to the test machine using a variety of interfaces and/or cables (e.g., serial, RS232, HDMI, etc.). In various embodiments, the test socket 94 and test board 96 are mounted to the platform 100 using a number of fasteners (e.g., screws).

In various embodiments, the platform 100 may comprise a controller 102, a moisture detector 104, and a transducer array 106. The controller 102 is generally configured to receive input from the moisture detector 104 and a voltage supply of the test machine 90. The controller 102 is further configured to provide control signals to the transducer array 106. The moisture detector 104 generally detects a level of moisture in the air surrounding the test system 90. In an example, the moisture detector 104 may be implemented as a humidistat configured to measure a relative humidity of the test environment. The transducer array 106 is enabled to generate ultrasonic vibrations in response to the control signal received from the controller 102. The control signals from the controller 102 to the transducer array 106 are generally configured to control a frequency and/or a strength (or amplitude) of the ultrasonic vibrations. The ultrasonic vibrations produced by the transducer array 106 are generally effective in preventing frost formation (e.g., nucleation, growth, etc.) between the test header 92 and a device under test located in the test socket 94. In an example, a frequency of the ultrasonic vibrations is selected for resonance with frost crystals to inhibit growth of the frost crystals.

Figure 4:
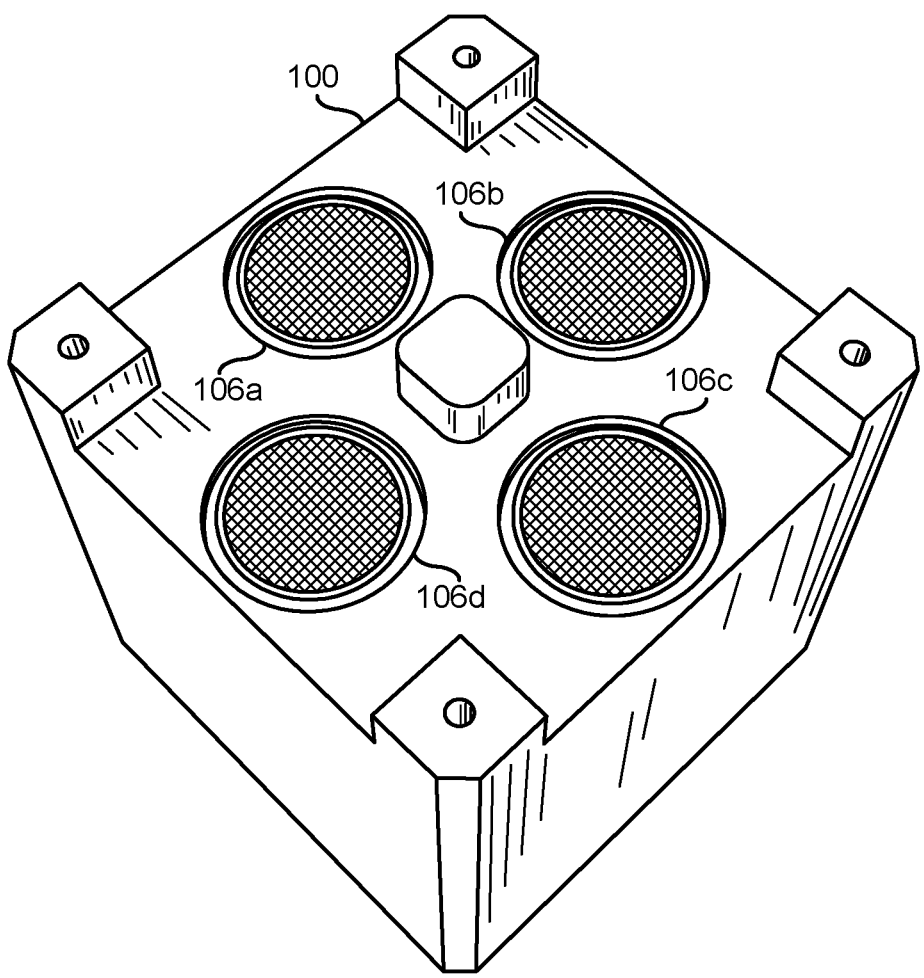
FIG. 4 is a diagram illustrating a transducer array of the platform of FIG. 3 in accordance with an example embodiment of the invention.

Referring to FIG. 4, a diagram is shown illustrating an upper surface of the platform 100. In various embodiments, the transducer array 106 may comprise a plurality of transducer elements. In an example, the number of transducer elements may be four (e.g., 106a-106d). The transducer elements 106a-106d are generally embedded in and distributed around the upper surface of a platform 100. The upper surface of the platform 100 may also include mounting points for attachment of the test board 96. In various embodiments, the test socket 94 and test board 96 may be attached to the platform 100 by screws passing through the test socket 94 and test board 96 and into the mounting points. In an example, the mounting points may be tapped with an appropriate thread or contain threaded inserts.

Figure 5:
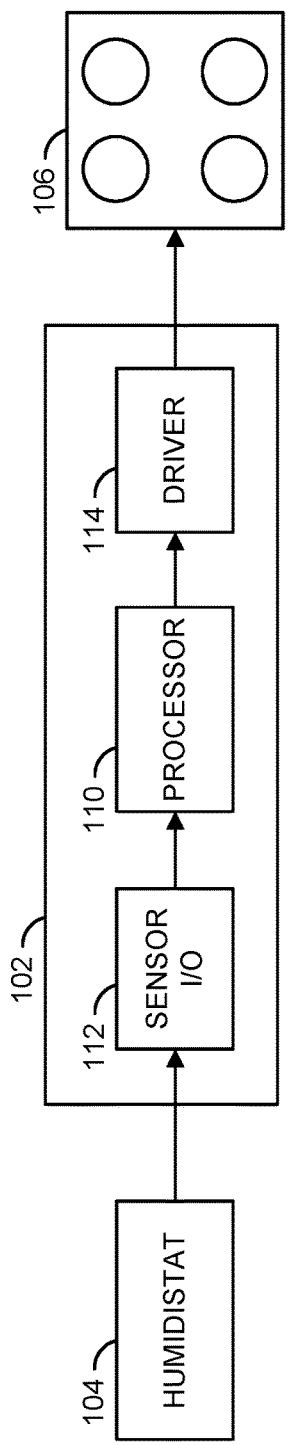
FIG. 5 is a block diagram illustrating an example embodiment of the invention.

Referring to FIG. 5, a block diagram is shown illustrating an example controller in accordance with an example embodiment of the invention. In various embodiments, the controller 102 may comprise a processor (e.g., CPU, MPU, etc.) 110, a sensor I/O block 112, and a driver block 114. The sensor I/O block 112 and the driver block 114 are generally connected to the processor 110. In various embodiments, the processor 110 may be implemented using one or more of analog and digital circuitry. In embodiments where the processor is implemented in analog circuitry, the processor may be implemented with predetermined thresholds at which an output level changes. In embodiments where the processor implements a digital controller, the connections may, for example, take the form of parallel signal lines. In another example, the connections may be implemented as one or more serial buses (e.g., I2C, etc.).

The sensor I/O block 112 may be configured to receive a signal or signals from the moisture detector 104. The sensor I/O block 112 may condition (e.g., amplify, digitize, etc.) the signal(s) received from the moisture detector 104 for presentation to the processor 110. The processor 110 may be configured to control the driver block 114 based on the signal(s) received from the sensor I/O block 112. In an example where, the transducer strength depends on supply voltage, the processor may control the voltage supply level of the transducer array 106. The driver block 116 may be configured to generate signals for controlling the transducer array 106 to generate ultrasonic vibrations having a desired frequency and/or strength. The processor 110 generally adjusts the signals presented to the ultrasonic array 106 by the driver block 114 based on input from the sensor I/O block 112.

Figure 6:
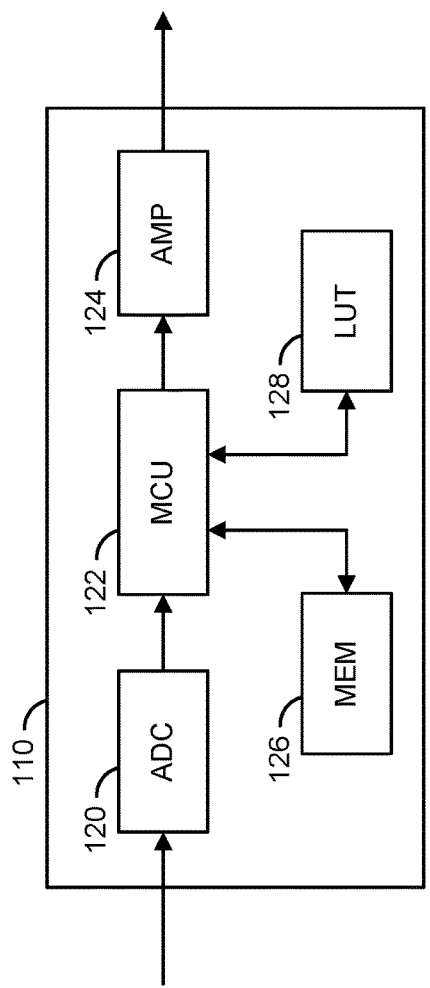
FIG. 6 is a block diagram illustrating an example implementation of a processor of FIG. 5 in accordance with an example embodiment of the invention.

Referring to FIG. 6, a diagram is shown illustrating an example implementation of the processor 110 of FIG. 5 in accordance with another example embodiment of the invention. In some embodiments, the processor 110 may comprise an analog to digital converter (ADC) block (or circuit) 120, a microcontroller (MCU) 122, an amplifier block (or circuit) 124, a memory block (or circuit 126), and a lookup table (LUT) 128.

The processor 110 may use the memory 126 to store program instructions and data. The program instructions may configure the microcontroller 122 to generate control signals for controlling the driver block 114 (e.g., via the amplifier 124) based upon information received by the microcontroller 122 from the sensor I/O block 112 (e.g., via the ADC 120). In an example, calculation of a frequency and/or a strength of the ultrasonic signal levels in response to the humidity measurements may be performed by program instructions and data stored in the memory 126. In an example, the lookup table (LUT) 128 may define a relationship between humidity measurements and defrosting power (e.g., frequency, strength, etc.) of the transducer array 106. In an example, the lookup table (LUT) 128 may be implemented separately from or as part of the memory 126. An example implementation of a lookup table may be summarized by the following TABLE 1:

TABLE 1

| HUMIDITY (RH %) | DEFROSTING STRENGTH |
| --- | --- |
| 5 | 50 |
| 10 | 50 |
| 15 | 50 |
| 20 | 50 |
| 25 | 50 |
| 30 | 50 |
| 35 | 50 |
| 40 | 50 |
| 45 | 50 |

TABLE 1-continued

| HUMIDITY (RH %) | DEFROSTING STRENGTH |
|---|---|
| 50 | 50 |
| 55 | 70 |
| 60 | 70 |
| 65 | 70 |
| 70 | 70 |
| 75 | 100 |
| 80 | 100 |
| 85 | 100 |
| 90 | 100 |
| 95 | 100 |
| 100 | 100 |

Figure 7:
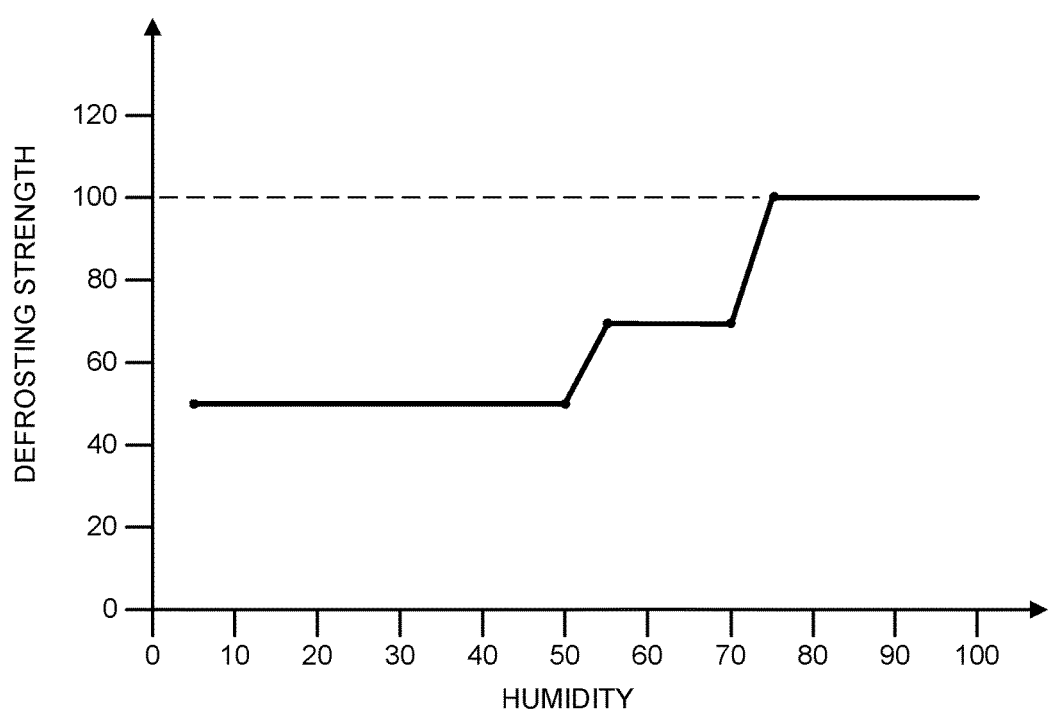
FIG. 7 is d diagram illustrating an example function for controlling defrosting strength based upon humidity statistics.

Referring to FIG. 7, a diagram is shown illustrating an example function curve for controlling defrosting strength based upon humidity statistics. In an example, a relationship between defrosting strength and humidity may be implemented as a continuous function similar to the discrete steps described in TABLE 1 above. In various embodiments, analog circuitry may be implemented with predetermined thresholds at which an output level changes. The circuitry may be configured to change the output level by predetermined amounts (or steps). In various embodiments, the number and value of the predetermined thresholds and amounts of the predetermined changes in the output level associated with the thresholds may be configured to meet design criteria of a particular implementation.

Figure 8:
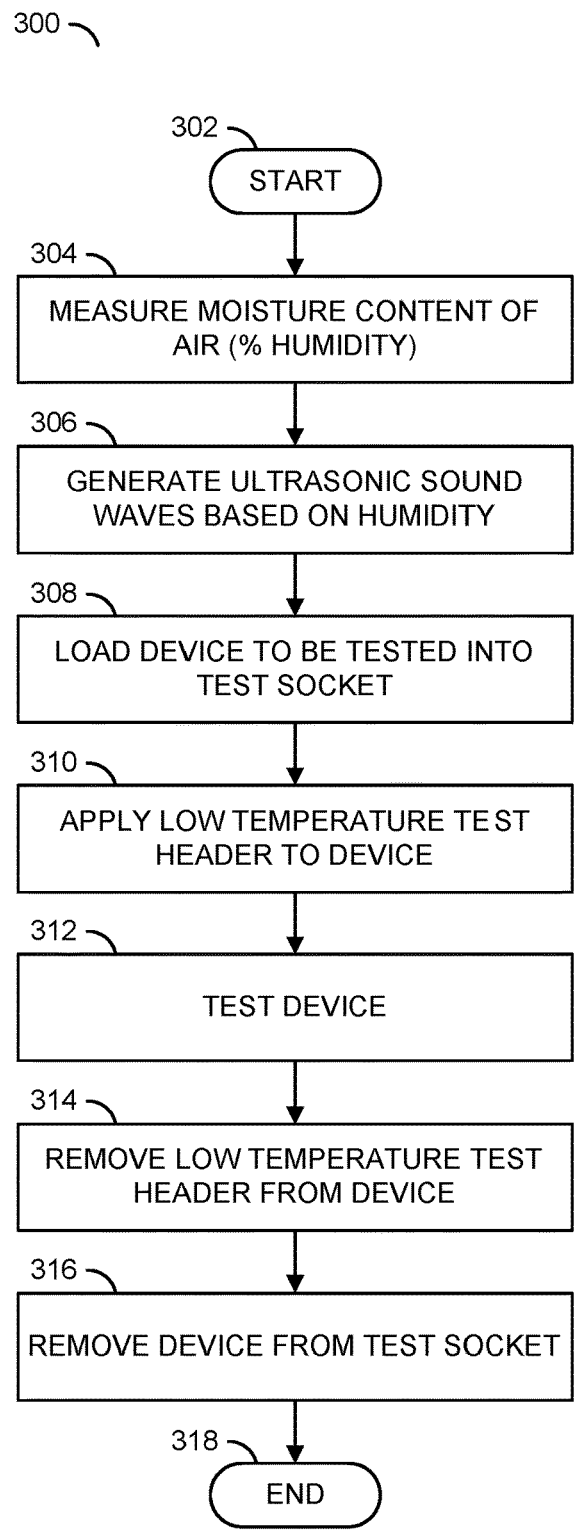
FIG. 8 is a flow diagram illustrating a test process in accordance with an example embodiment of the invention.

Referring to FIG. 8, a flow diagram illustrating a test process in accordance with an example embodiment of the invention. In one example, a process (or method) 300 may be implemented during a low temperature test of a semiconductor device. The process 300 may include a step (or state) 302, a step (or state) 304, a step (or state) 306, a step (or state) 308, a step (or state) 310, a step (or state) 312, a step (or state) 314, a step (or state) 316, and a step (or state) 318. The process 300 may start in the step 302. In the step 304, the process 300 may make a measurement of the moisture content of the air around a test system. In one example, the measurement may be a relative humidity. The relative humidity may be expressed as a percentage.

In the step 306, the process 300 may begin generating ultrasonic vibrations to inhibit frost formation. In the step 308, the process 300 may load a semiconductor device to be tested into the test socket 94. In an example, the device under test (DUT) may be loaded into the test socket 94 manually. In another example, the DUT may be loaded into the test socket 94 using a pick and place handler. In the step 310, the process 300 may apply the test header 92 to the device under test. The process 300 generally provides low temperature test conditions to the device under test via the test header 92. In some embodiments using a pick and place handler, the pick and place handler may comprise the test header 92. In some embodiments, the pick and place handler and the test header 92 may be separate.

In the state 312, the process 300 may test the semiconductor device by applying test signals to the device and receiving test responses from the device via the test socket 94 and test board 96. In the state 314, the process 300 may remove the low temperature test header 92 from the device. In the state 316, the process 300 may remove the semiconductor device from the test socket 94. The process 300 may then move to the step 318 and terminate, or the process 300 may return to the step 308 to repeat the steps for other devices to be tested.

In various embodiments, a test apparatus in accordance with an example embodiment of the invention may adopt a defrosting controller that utilizes an ultrasonic transducer to effectively restrain (inhibit) the initial frost nucleation and frost growth processes between a chilled test header and a semiconductor device under test. The defrosting strength may be controlled by the defrosting controller based on humidity statistics obtained from a humidity monitor (e.g., humidistat). In another aspect, embodiments may provide a method for enhancing semiconductor device testing in low temperature conditions. In various embodiments, stability and throughput of semiconductor device testing is increased, while retaining the robustness of the test device and the handler.

The terms "may" and "generally" when used herein in conjunction with "is(are)" and verbs are meant to communicate the intention that the description is exemplary and believed to be broad enough to encompass both the specific examples presented in the disclosure as well as alternative examples that could be derived based on the disclosure. The terms "may" and "generally" as used herein should not be construed to necessarily imply the desirability or possibility of omitting a corresponding element.

While the invention has been particularly shown and described with reference to embodiments thereof, it will be understood by those skilled in the art that various changes in form and details may be made without departing from the scope of the invention.

The invention claimed is:

1. An apparatus comprising:
   a platform comprising (i) a sensor configured to measure moisture content of air around said platform, (ii) a transducer array configured to generate ultrasonic vibrations, and (iii) a controller configured to control said transducer array based on measurements of said moisture content;
   a test board mounted on the platform; and
   a test socket attached to the test board, wherein the test socket is configured to apply test signals to and receive test responses from a semiconductor device under test, and the platform is configured to utilize said ultrasonic vibrations to inhibit frost formation between the semiconductor device under test and a test header providing a low temperature test condition.

2. The apparatus according to claim 1, wherein said sensor comprises a humidistat.

3. The apparatus according to claim 1, wherein said transducer array comprises a plurality of ultrasonic transducers.

4. The apparatus according to claim 1, wherein said controller is configured to adjust a frequency, an amplitude, or both the frequency and the amplitude of the ultrasonic vibrations based on said moisture content.

5. The apparatus according to claim 1, wherein said controller is configured to adjust a supply voltage of said transducer array in response to a measured amount of moisture in the air around said platform.

6. The apparatus according to claim 1, wherein said controller comprises an analog circuit configured to generate an output voltage as a function of said moisture content.

7. The apparatus according to claim 1, wherein said controller comprises:
   an analog to digital converter configured to convert said measurements of said moisture content to digital values; and
   a microcontroller configured to generate one or more control signals in response to the digital values, wherein the one or more control signals control an ultrasonic driver strength of said transducer array.

8. The apparatus according to claim 7, wherein said microcontroller is further configured to generate said one or more control signals based upon values in a lookup table.

9. An apparatus comprising a plurality of test assemblies, each test assembly comprising:
- a respective platform comprising (i) a sensor configured to measure moisture content of air around said respective platform, (ii) a transducer array configured to generate ultrasonic vibrations, and (iii) a controller configured to control said transducer array based on measurements of said moisture content;
- a respective test board mounted on the respective platform; and
- a respective test socket attached to the respective test board, wherein the respective test socket is configured to apply test signals to and receive test responses from a semiconductor device under test, and the respective platform is configured to utilize said ultrasonic vibrations to inhibit frost formation between the semiconductor device under test and a test header providing a low temperature test condition.

10. A method of enhancing semiconductor device testing in low temperature conditions comprising:
- measuring a moisture content of air around a test system;
- placing said semiconductor device to be tested into a test socket;
- applying said low temperature conditions to the semiconductor device under test via a test header; and
- generating ultrasonic vibrations based on the moisture content measured while testing the semiconductor device, wherein (i) the ultrasonic vibrations inhibit frost formation between the semiconductor device under test and the test header and (ii) generating said ultrasonic vibrations based on the measured moisture content comprises using an analog circuit to generate a drive voltage for an ultrasonic transducer array as a function of the measured moisture content.

11. The method according to claim 10, wherein the moisture content is measured as a relative humidity.

12. The method according to claim 10, wherein said test header is manually placed on said semiconductor device.

13. The method according to claim 10, wherein said semiconductor device is manually placed in said test socket.

14. The method according to claim 10, wherein said semiconductor device is loaded in said test socket by a pick and place handler.

15. The method according to claim 14, wherein said test header is part of said pick and place handler.

16. A method of enhancing semiconductor device testing in low temperature conditions comprising:
- measuring a moisture content of air around a test system;
- placing said semiconductor device to be tested into a test socket;
- applying said low temperature conditions to the semiconductor device under test via a test header; and
- generating ultrasonic vibrations based on the moisture content measured while testing the semiconductor device, wherein (i) the ultrasonic vibrations inhibit frost formation between the semiconductor device under test and the test header and (ii) generating said ultrasonic vibrations based on the measured moisture content comprises:
- using an analog to digital converter to convert measurements of said moisture content to digital values; and
- using a microcontroller to generate one or more control signals in response to the digital values, wherein the one or more control signals control an ultrasonic driver strength of an ultrasonic transducer array.

17. The method according to claim 16, wherein said microcontroller is configured to generate said one or more control signals based upon values in a lookup table.

18. The method according to claim 10, further comprising adjusting a frequency of said ultrasonic vibrations for resonance with frost crystals of a predetermined size.

* * * * *